United States Patent [19]

Cirera et al.

[11] Patent Number: 4,835,156
[45] Date of Patent: May 30, 1989

[54] VASODILATORY DIHYDRODIBENZOCYCLOHEPTYLIDEN-ETHYL PIPERAZINE DERIVATIVES AND PROCESS FOR THE PREPARATION OF THESE COMPOUNDS

[75] Inventors: Xavier D. Cirera; Romeo R. Andreoli; Pedro P. Lloveras; Leonida Bruseghini; Jose P. Irrure, all of Barcelona, Spain

[73] Assignee: Sociedad Espanola De Especialidades Terepeuticas, S.A., Barcelona, Spain

[21] Appl. No.: 54,408

[22] Filed: May 26, 1987

Related U.S. Application Data

[63] Continuation-in-part of Ser. No. 635,898, Jul. 30, 1984, abandoned.

[30] Foreign Application Priority Data

Aug. 2, 1983 [ES] Spain ................................ 524680

[51] Int. Cl.⁴ .......................................... A61K 31/645
[52] U.S. Cl. ........................................ 514/255; 544/380
[58] Field of Search ....................... 514/255; 544/380

[56] References Cited

U.S. PATENT DOCUMENTS 3,906,110  9/1975  Francis ................................ 564/319
4,381,305  4/1983  Casagrande ......................... 514/357

FOREIGN PATENT DOCUMENTS 2279389  2/1976  France .
49-43953  4/1974  Japan .
49-108053  10/1974  Japan .
52-105155  9/1977  Japan .
6507535  12/1966  Netherlands .
1128938  10/1968  United Kingdom .

OTHER PUBLICATIONS

Chemical Abstracts 93: 197538f (1980).
Chemical Abstracts 84: 164397v (1976).
Plilai, Agents Acting on the Central Nervous System: part XXVI; Indian J. Chem. vol. 14B, Sep. 1976; pp. 714–716.
Chemical Abstracts 81: 120194k (1974).

*Primary Examiner*—C. Warren Ivy
*Attorney, Agent, or Firm*—Michael J. Striker

[57] ABSTRACT

A dihydrodibenzocycloheptyliden-ethyl-piperazine derivative of the general formula:

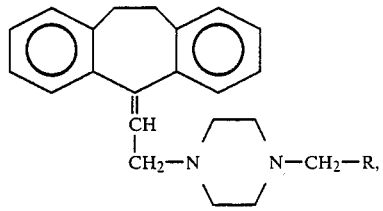

in which,
R = —CH=CH$_2$; —CH$_2$OH; —COOH; —CO$_2$C$_2$H$_5$;
—CH=CH—CO$_2$CH$_3$; —CH=CH—CO$_2$CH$_3$,
—C$_6$H$_5$,

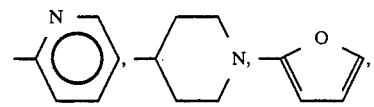

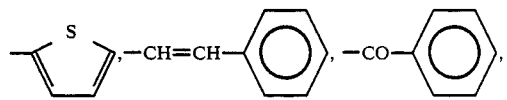

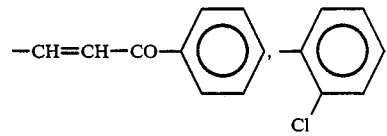

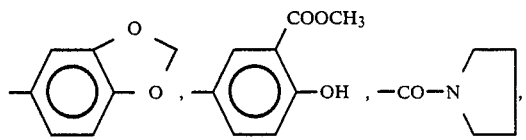

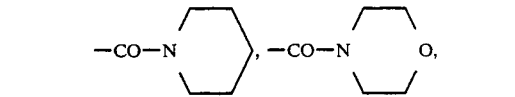

—CO—NH or —(CONH)$_2$—CH$_2$,

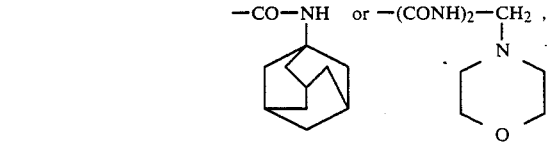

or pharmaceutically acceptable salts thereof, are disclosed. The compounds of the invention are useful in pharmaceutical compositions for the treatment of pathologies responsive to vasodilatory agents.

4 Claims, No Drawings

VASODILATORY DIHYDRODIBENZOCYCLOHEPTYLIDEN-ETHYL PIPERAZINE DERIVATIVES AND PROCESS FOR THE PREPARATION OF THESE COMPOUNDS

CROSS-REFERENCE TO RELATED APPLICATION

This application is a continuation-in-part of application Ser. No. 635,898, filed July 30, 1984, now abandoned.

BACKGROUND OF THE INVENTION

The invention concerns pharmacologically active compounds derived from dihydrodibenzocycloheptylidenethylpiperazine, useful in the treatment of pathologies responsive to vasodilatory agents.

Many agents displaying such activity are known. For example, cinarizine and flunarizine are antiulcer agents. However, the activity of these agents is not always satisfactory.

It is therefore an object of the present invention to provide new pharmacologically active compounds displaying this activity.

SUMMARY OF THE INVENTION

This object is attained according to the present invention by novel compounds derived from dihydrodibenzocyclohepyliden-ethylpiperazine of the general formula (I-B)

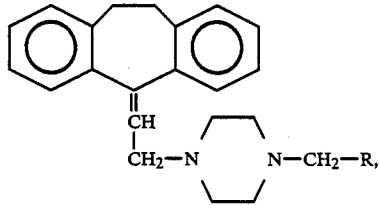

(I-B)

wherein,
R=—CH=CH$_2$; —CH$_2$OH; —COOH; —CO$_2$C$_2$H$_5$; —CH=CH—CO$_2$CH$_3$;

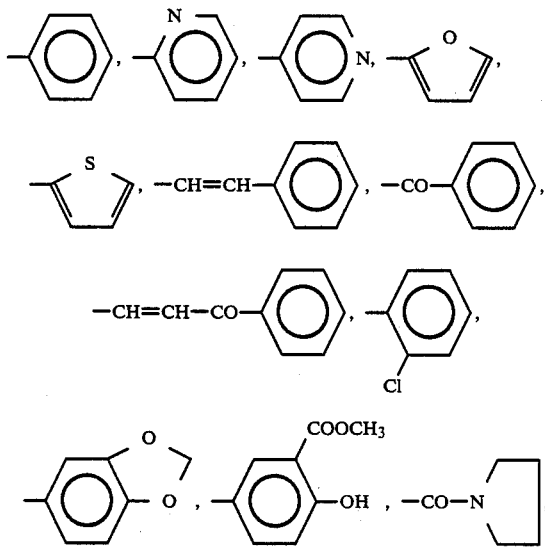

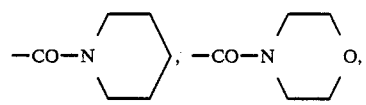

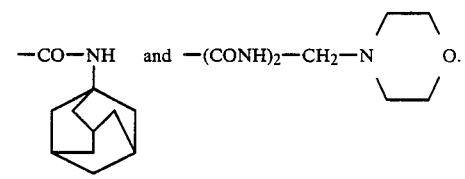

Salts and other derivatives of the compounds of Formula I-B, likewise of pharmacological interest, such as N-oxides and quaternary ammonium salts are also included within the scope of the present invention, as well as the process for the production of said compounds and their derivatives, and therapeutic applications of the same.

The compounds according to the present invention possess a marked vasodilatory activity, as will be set forth further below.

The compounds defined by the general formula I-B are prepared by reacting an piperazine of general formula II-B

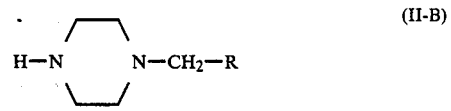

(II-B)

wherein R is the same as defined for general formula I-B, with a halogen derivative of the formula III-B

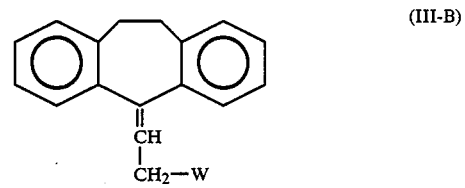

(III-B)

wherein, W is a chlorine or bromine atom.

The reaction is carried out in an inert solvent and in the presence of a hydrogen halide binder, which may be an inorganic or organic base, or an excess of the original amine. The compounds of general formula I-B may also be prepared by reacting the piperazine of formula IV-B

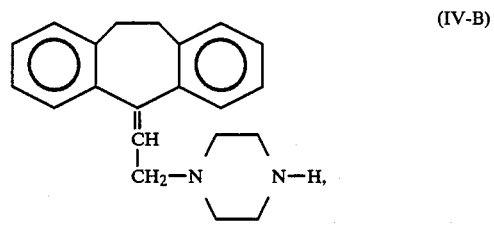

(IV-B)

with a halogen derivative of the general formula W—CH$_2$—R, wherein W and R are the same as before.

The reaction is carried out in the same conditions as before.

Finally, the compounds of general formula I-B may also be prepared by reacting the aldehyde of formula V-B

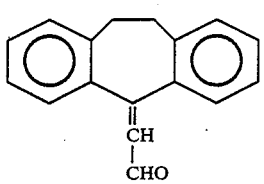
(V-B)

with a piperazine of the general formula II-B (as before), in the presence of a reducing agent such as sodium borohydride or catalytic hydrogenation.

An alternative form for the compounds of formula I-B includes salts thereof with minimal acids, such as, for example, hydrochloric, sulfuric or nitric acid, or with organic acids, such as, for example, oxalic, salycylic, citric, maleic or fumaric acid. The employment of hydrochloric or maleic acid is, however, preferable, due to their favorable pharmacological properties.

In the embodiments which follow, the compounds of formula I-B are designated for purposes of simplicity by the alphabetic expression "WAS-..." followed by a number which is exclusive for the specific combination of substituent choices as set forth.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Examples 1 and 2 show chemical synthesis of the compounds according to the present invention:

EXAMPLE 1

Preparation of N-benzyl-N'-2-(10,11-dihydrodibenzo-(a,d)-cyclohept-5-yliden)-ethyl piperazine This compound is designated as WAS-4206.

A mixture of 5.10 g (20 mmoles) of 2-chloro-1-(10,11-dihydrodibenzo-(a,d)-cyclohept-5-yliden)-ethane and 3.52 g (20 mmoles) of N-benzylpiperazine is refluxed in 100 ml of acetonitrile for 4 hours in the presence of 2.52 g (3 mmoles) of sodium bicarbonate The mixture is then cooled and filtered followed by elimination of the solvent and recrystallization of the residue from 10 ml of acetone. In this manner, 3.78 g of N'-2-(10,11-dihydro-dibenzo-(a,d)-cyclohept-5-yliden-)ethylpiperazine are obtained.

Yield: 48%.

Analytical data:

| Melting point: | 128–130° C. |
|---|---|
| IR: | 3055, 3015, 2930, 2800, 1600, 1485, 1450, 1145, 1010, 770, 755, 740 and 700. |
| NMR: | 7.25/sc(13H); 6.0/t(1H); 3.50/t(2H); 3.10/sc(8H); 2.5/s(4H); 2.35/sc(2H) |

EXAMPLE 2

Preparation of N-2-(10,11-dihydrobenzo-(a,d)-cyclohept-5-yliden)-ethyl-N'-(2-thenyl)-piperazine This compound is briefly designated as WAS-4226.

A mixture of 5.10 g (20 mmoles) of 2-chloro-1-(10,11-dihydrodibenzo-(a,d)cyclohept-5-ylidene)-ethane and 3.64 g (20 mmoles) of N-2-thenylpiperazine is refluxed in 100 ml of chloroform for 6 hours in the presence of 2.52 g (30 mmoles) of sodium bicarbonate.

The mixture is cooled and filtered, and the solvent is eliminated, after which the residue is suspended in 50 ml of acetone and treated with an excess of saturated maleic acid in acetone. The precipitate is filtered and recrystallized from water. A product of 6.24 g of N-2-(10,11-dihydrodibenzo-(a,d)-cyclohept-5-yliden)-ethyl-N'-2-(thenyl)piperazine associated at 1:2 with maleic acid is obtained.

Yield: 50%.

| Melting point: | 202° C. (decomposition) |
|---|---|
| IR: | 3070, 3010, 1690, 1625, 870, 775, 760, 745 and 650. |
| NMR: | 8.8/sc(4H); 7.6/sc(1H); 7.3/t(10H); 6.25/s(1H); 6.05/s(1H); 2.5–4.0/sc(16H) |

EXAMPLE 3

Preparation of N-benzyl-N'-2-(10,11-dihydrodibenzo-(a-d)-cyclohept-5-yliden)-ethylpiperazine (WAS-4206)

A mixture of 6.08 g (20 mmoles) of N-2-(10,11-clihydrodibenzo-(a,d)-cyclohept-5-yliden)ethylpiperazine and 2.53 g (20 mmoles) of benzyl chloride in 100 ml of acetonitrile is heated under reflux for 6 hours in the presence of 2.52 g (30 mmole) of sodium bicarbonate. Working-up as in Example 1 yields 3.54 g of WAS-4206 (Yield: 45%). The analytical data are the same as for Example 1.

EXAMPLE 4

Preparation of N-2-(10,11-dihydrodibenzo-(a,d)-cyclohept-5-yliden)-ethyl-N'-(2-thenyl)-piperazine (WAS-4226)

A mixture of 4.68 g (20 mmole) of (10,11-dihydrodibenzo-(a,d)-cyclohept-5-yliden)ethanal and 3.64 g (20 mmoles) of N-2-thenyl-piperazine in 100 ml of methanol is treated with 0.76 g (20 mmoles of sodium borohydride in 10 ml of methanol.

Working up is as in Example 2 yields 6.86 g of WAS-4226 dimaleate. (Yield: 55%).

The analytical data are the same as for Example 2.

In Table 1 some columns are headed by alphabetical signs, with the following significance:

| Column A = | No. of Example |
|---|---|
| Column B = | Brief denomination of the compound obtained and analyzed. |
| Column C = | Indicates the number corresponding to the former Example (1 or 2) in which the method of preparation has been described in detail. |
| Column D = | Melting point in degrees C. |

TABLE 1
| A | B | R | C | D | Analytical Data NMR |
|---|---|---|---|---|---|
| Ex. 10 | WAS-4207 | CH=CH—C₆H₅ | 1 | 120–122 | 7.2/sc(13); 5.5–6.1/sc(3); 2.5–3.7/sc(16) |
| Ex. 21 | WAS-4220 | 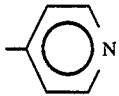 | 2 | 144 (*) | 8.55/d(2); 7.45/d(2); 7.1/sc(8) 6.0/t(1); 2.5–4.0/sc(16) |
| Ex. 22 | WAS-4221 | 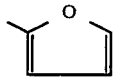 | 2 | 189 (*) | 7.6/sc(1); 7.2/sc(10); 6.0/t(1); 2.5–4.0/sc(16) |
| Ex. 23 | WAS-4222 | 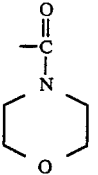 | 2 | 192 (*) | 7.2/sc(8); 5.95/t(1); 2.5–3.75/sc(22) |
| Ex. 24 | WAS-4223 | 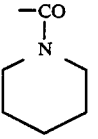 | 2 | 178 (*) | 7.25/sc(8); 6.0/t(1); 1.5–4.0/sc(26) |
| Ex. 25 | WAS-4224 | 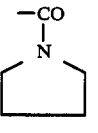 | 2 | 186 (*) | 7.15/sc(8); 5.9/t(1); 1.6–3.7/sc(24) |
| Ex. 26 | WAS-4225 | —CH=CH₂ | 2 | 179 (*) | 7.25/sc(8); 5.3–6.1/sc(4); 2.3–3.7/sc(16) |
| Ex. 27 | WAS-4227 |  | 2 | 161 (*) | 8.6/sc(2); 7.8/sc(2); 7.25/sc(8) 6.0/t(1); 2.5–3.7/sc(16) |
| Ex. 29 | WAS-4229 | —CH₂OH | 2 | 159 (*) | 8.5/sa(1); 7.15/sc(8); 6.0/t(1); 2.5–4.0/sc(18) |
| Ex. 31 | WAS-4231 | CH₃CH₂O—C=O | 2 | 181 (*) | 7.25/sc(8); 6.0/t(1); 1.8–4/sc(21) |
| Ex. 32 | WAS-4232 | 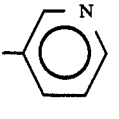 | 2 | 148 (*) | 7.7–8.5/sc(4); 7.2/sc(8); 6.0/t(1); 2.5–4.0/sc(16) |
| Ex. 33 | WAS-4233 | —COOH | 2 | 197 (*) | 7.15/sc(8); 6.0/t(1); 2.5–3.5/sc(19) |
| Ex. 34 | WAS-4234 | 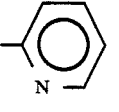 | 2 | 191 (*) | 7.6/sc(1); 7.2/sc(10); 6.0/t(1); 2.5–4/sc(16) |
| Ex. 37 | WAS-4237 | —CH=CH—COOCH₃ | 2 | 178 (*) | 7.25/sc(8); 5.5–6.1/sc(3); 2.5–4/sc(19); |
| Ex. 38 | WAS-4238 | Cl—C₆H₅ | 2 | 183 (*) | 7.2/sc(12); 6.0/t(1); 2.5–4/sc(16) |

TABLE 1-continued

| | | | | Analytical Data | |
|---|---|---|---|---|---|
| A | B | R | C | D | NMR |
| Ex. 39 | WAS-4239 | (1-adamantyl)-NH-C(=O)- | 2 | 160 (*) | 7.2/sc(8); 5.9/t(1); 4.9/sa(1); 2.5–4/sc(16); 1.6/sc(15) |
| Ex. 72 | WAS-4601 | -CONH-CO-NH-CH$_2$-N(morpholine) | 2 | 105 (*) | 8.3/sa(2); 7.2/sc(8); 6.0/t(1); 2.5–4.0/sc(26) |
| Ex. 73 | WAS-4602 | C$_6$H$_5$-C(=O)-CH$_2$- | 2 | 176 (*) | 7.2/sc(13); 6.0/t(1); 2.5–4.0/sc(16) |
| Ex. 74 | WAS-4604 | -C$_6$H$_3$(OH)(COOCH$_3$)- | 2 | 186 (*) | 9.5/sa(1); 7.5/sc(1); 7.2/sc(10); 6.0/t(1); 2.5–4/sc(19) |
| Ex. 75 | WAS-4605 | -CH=CH-C(=O)-C$_6$H$_5$ | 2 | 172 (*) | 7.2/sc(13); 5.4–6.1/sc(3); 2.5–4.0/sc(16) |

PHARMACOLOGICAL PROPERTIES

The compounds according to the present invention possess vasodilatory activity. What follows is a description of the methods used for evaluation of the above-mentioned pharmacological activity, together with the results obtained with the most representative compounds among those according to the present invention.

Vasodilatory Activity

The results corresponding to this trial are shown in Tables 2 and 3, which follow.

The results have been expressed symbolically by crosses, the number of which being proportional to the intensity of effect, with the maximum value of four crosses representing an intensity of action comparable to the standard drug used. The significance of the symbols is as follows:

++++ Very intense activity
+++ Considerable activity
++ Low activity
+ Low activity
0 Null activity In order to test the vasodilatory activity, the first trial employs the technique of the isolated rat hind-quarters (Table 2), which involves antagonizing the vasoconstrictive effect of perfusion of hyperkalaemic Tyrode solution, according to the method of F. N. Fastier and F. H. Smirk (J. Pharm. Exp. Therap. 89, 256–170 (1947)), and then calculating for the products which show the greatest activity, the ED$_{30}$, that is the dose which produces a 30% vasodilatory activity with respect to the basic vasoconstriction.

For the remaining, less active products, the activity is expressed in the form of crosses with respect to the standard drugs, in this case, cinnarizine and flunarizine.

TABLE 2

| Compound | Compound Described in Example No. | Vasodilatory Activity (Rat hind-quarters) | |
|---|---|---|---|
| | | Evaluation | ED$_{30}$ × 10$^{-5}$ × 10 M |
| WAS-4206 | 1 and 3 | ++++ | 1.93 |
| WAS-4207 | 10 | ++++ | 2.17 |
| WAS-4220 | 21 | 0 | — |
| WAS-4221 | 22 | 0 | — |
| WAS-4222 | 23 | + | — |
| WAS-4223 | 24 | 0 | — |
| WAS-4224 | 25 | 0 | — |
| WAS-4225 | 26 | ++++ | 1.46 |
| WAS-4226 | 2 and 4 | 0 | — |
| WAS-4227 | 27 | + | — |
| WAS-4229 | 29 | 0 | — |
| WAS-4231 | 31 | ++ | — |
| WAS-4232 | 32 | ++ | — |
| WAS-4233 | 33 | 0 | — |
| WAS-4234 | 34 | 0 | — |
| WAS-4237 | 37 | ++++ | 4.23 |
| WAS-4238 | 38 | 0 | — |
| WAS-4239 | 39 | ++ | — |
| WAS-4601 | 72 | ++++ | 4.33 |
| WAS-4602 | 73 | 0 | — |
| WAS-4604 | 74 | + | — |
| WAS-4605 | 75 | ++++ | 2.97 |
| The results obtained with standard drugs are as follows: | | | |
| Cinnarizine | | ++++ | 1.51 |
| Flunarizine | | ++++ | 3.47 |

In a further trial, the vasodilatory activity is evaluated by the technique of vasodilation in perfused rabbit cerebral territory as described by P. Vaupel and H. Hutten (Arzneim. Forsch./Drug Res. 30(I), 598–602 (1980)), calculating the variation in perfusion pressure after treatment (Table 3).

Table 3 employs the same conventional signs based on crosses, with the same relative significance as in Table 2.

The standard drug employed is cinnarizine.

TABLE 3

| Compound | Compound Described in Example No. | Vasodilatory Activity (Rabbit cerebral territory) Evaluation | Vasodilatory Index (*) (mm$^2$) |
|---|---|---|---|
| WAS-4206 | 1 and 3 | ++ | 285.3 |
| WAS-4207 | 10 | 0 | 16.2 |
| WAS-4220 | 21 | ++++ | 1159.2 |
| WAS-4221 | 22 | +++ | 321.4 |
| WAS-4222 | 23 | ++++ | 454.6 |
| WAS-4223 | 24 | ++++ | 1133.6 |
| WAS-4224 | 25 | +++ | 342.0 |
| WAS-4225 | 26 | 0 | 0 |
| WAS-4226 | 2 and 4 | 0 | 74.0 |
| WAS-4227 | 27 | ++ | 253.7 |
| WAS-4229 | 29 | 0 | 55.6 |
| WAS-4231 | 31 | 0 | 0 |
| WAS-4232 | 32 | 0 | 46.8 |
| WAS-4233 | 33 | 0 | 0 |
| WAS-4234 | 34 | 0 | 0 |
| WAS-4237 | 37 | 0 | 19.6 |
| WAS-4238 | 38 | 0 | 0 |
| WAS-4239 | 39 | 0 | 0 |
| WAS-4601 | 72 | + | 180.8 |
| WAS-4602 | 73 | +++ | 378.3 |
| WAS-4604 | 74 | 0 | 20.0 |
| WAS-4605 | 75 | ++++ | 420.9 |
| The result obtained with the standard drug is as follows: | | | |
| Cinnarizine | | ++++ | 535.0 |

(*) Calculated by multiplying the % vasodilation by duration of action.

Toxicity

Table 4 sets forth the results of the indicative LD$_{50}$ for the most representative of the compounds according to the present invention.

The compounds are administered by the intraperitoneal route to Swiss mice, after which the toxic effects are observed, and the mortality rate and the LD$_{50}$ 7 days post-administration are calculated.

TABLE 4

| Compound | Compound Described in Example No. | Indicative LD$_{50}$ mg/kg i.p. |
|---|---|---|
| WAS-4206 | 1 and 3 | 880 |
| WAS-4207 | 10 | 925 |
| WAS-4220 | 21 | 185 |
| WAS-4221 | 22 | 185 |
| WAS-4222 | 23 | 185 |
| WAS-4223 | 24 | 185 |
| WAS-4224 | 25 | 385 |
| WAS-4225 | 26 | 175 |
| WAS-4226 | 2 and 4 | 385 |
| WAS-4227 | 27 | 175 |
| WAS-4229 | 29 | 115 |
| WAS-4231 | 31 | 175 |
| WAS-4232 | 32 | 115 |
| WAS-4233 | 33 | 900 |
| WAS-4234 | 34 | 600 |
| WAS-4237 | 37 | 3000 |
| WAS-4238 | 38 | 340 |
| WAS-4239 | 39 | 340 |
| WAS-4601 | 72 | 125 |
| WAS-4602 | 73 | 200 |

TABLE 4-continued

| Compound | Compound Described in Example No. | Indicative LD$_{50}$ mg/kg i.p. |
|---|---|---|
| WAS-4604 | 74 | 900 |
| WAS-4605 | 75 | 115 |

Therapeutical Applications

The compound described in the present invention have the following therapeutical applications:

Treatment and prophylaxis of cerebral circulatory insufficiency; cerebral vascular accidents, hemiplegic sequaelae, prevention of relapse; dizzy spells and Meunier-type syndromes; protection of the brain against endogenous, toxic, endocrine, infections and drug-induced aggressions;

complementary treatment of arterial hypertension; prevention of capillary fragility and hyperpermeability; basic treatment of geriatric cerebral vascular pathology; peripheral vascular disorders; generalized arteriosclerosis and its symptoms; opthalmic and vestibular vascular disorders.

PHARMACEUTICAL FORMS AND DOSAGE

All of the compounds according to the present invention can be administered by means of all the pharmaceutical forms compatible with their pharmacotechnical and therapeutic properties, at an adequate dosage. This includes tablets, dragees, pills, capsules, powders, lozenges, syrups and the like for oral administration, suppositories for rectal administration, and injection solutions for parenteral administration. The daily dose of the active pharmaceutical product may vary over a wide margin between 0.1 mg and 1,500 mg depending on the therapeutic application and the form of administration.

While the invention has been illustrated and described as embodied in dihydrodibenzocycloheptyliden-ethyl-piperazine derivatives and process for preparation thereof, it is not intended to be limited to the details shown, since various modifications and structural changes can be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims.

What is claimed is:

1. A dihydrodibenzocycloheptyliden-ethylpiperazine derivative of the formula:

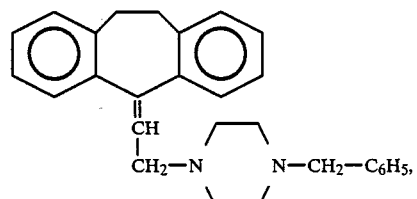

or a salt thereof.

2. The dihydrodibenzocycloheptyliden-ethylpiperazine derivative according to claim 1, wherein said salt is selected from the group consisting of an N-oxide and a quaternary ammonium salt.

3. A pharmaceutical composition for use in the treatment of pathologies responsive to vasodilatory agents containing, as an active ingredient, at least one compound recited in claim 1.

4. A process for the treatment of a pathological condition responsive to a vasodilatory agent by administration of an effective amount of the pharmaceutical composition of claim 3.

* * * * *

UNITED STATES PATENT AND TRADEMARK OFFICE
CERTIFICATE OF CORRECTION

PATENT NO. : 4 835 156

DATED : May 30, 1989

INVENTOR(S) : Xavier D. Cirera, Romeo R. Andreoli, Pedro P. Lloveras, Leonida Bruseghini, Jose P. Irrure It is certified that error appears in the above-identified patent and that said Letters Patent is hereby corrected as shown below:

On the title page:

In the heading [73[, the name of the assignee should read:

--Sociedad Espanola de Especialidades Farmaco-Terapeuticas, S.A.--

Signed and Sealed this

Fourth Day of June, 1991

Attest:

HARRY F. MANBECK, JR.

Attesting Officer

Commissioner of Patents and Trademarks